United States Patent
Zentgraf et al.

(10) Patent No.: US 7,029,866 B1
(45) Date of Patent: Apr. 18, 2006

(54) CANCER DIAGNOSIS BY THE MEASUREMENT OF NUP88 IN BODY SAMPLES

(76) Inventors: Hanswalter Zentgraf, Bluntschlistr. 6, 69115 Heidelberg (DE); Susanne Franz, Neugattiling 52, Neugärteuring 52 (DE); Angel Alonso, Adenaver-Ring 48, 69214 Eppelheim (DE); Nerea Martinez, Surkijo, 11, 48930 Las Arenas-Vizcaya (ES)

( * ) Notice: Subject to any disclaimer, the term of this patent is extended or adjusted under 35 U.S.C. 154(b) by 627 days.

(21) Appl. No.: 09/684,890

(22) Filed: Oct. 10, 2000

(51) Int. Cl.
*G01N 33/574* (2006.01)

(52) U.S. Cl. .................. 435/7.23; 530/350; 530/387.3; 530/387.7; 530/387.9; 530/388.8; 435/330; 435/331; 536/24.31; 536/24.33; 436/64

(58) Field of Classification Search ................ 435/330, 435/331, 7.23; 530/350, 387.3, 387.9, 389.7, 530/388.8, 387.7; 536/24.31, 24.33; 436/64; 424/9.1
See application file for complete search history.

(56) References Cited

U.S. PATENT DOCUMENTS

| | | | | |
|---|---|---|---|---|
| 5,356,817 A | * | 10/1994 | Cole | 436/510 |
| 5,366,866 A | * | 11/1994 | Xu et al. | 435/7.23 |
| 5,585,089 A | * | 12/1996 | Queen et al. | |
| 6,312,908 B1 | * | 11/2001 | Wahl et al. | 435/6 |
| 6,441,143 B1 | * | 8/2002 | Koski | 530/388.85 |
| 6,682,901 B1 | * | 1/2004 | Blaschuk et al. | 435/7.23 |

OTHER PUBLICATIONS

Campbell AM. Monoclonal Antibody Technology, Laboratory Techniques in Biochemistry and Molecular Biology, Elsevier Science Publishers B.V.: Amsterdam, The Netherlands, vol. 13, pp. 1-32.*
Fornerod M, et al. Genomics. 1997; 42: 538-40.*
Fornerod M, et al. EMBO J. Feb. 17, 1997; 16 (4): 807-16.*
Mariuzza RA, et al. Annu Rev Biophys Biophys Chem. 1987; 16: 139-59.*
Gould VE, et al. Am J Pathol. Nov. 5, 2000; 157 (5): 1605-13.*
Boer JM, et al. Exp Cell Res. 1997; 232: 182-5.*
Bastos R, et al. J Cell Biol. Jun. 2, 1997; 137 (5): 989-1000.*
Matsuoka Y, et al. Biochem Biophys Res Commun. 1999; 254: 417-23.*
Alberts et al (Molecular BIology of the Cell, 3rd Ed., 194, p. 465).*
Shantz and Pegg (Int J. of BIochem and Cell Biol., 1999, 31:107-122).*
McClean and Hill (Eur. J. Can, 1993, 29A:2243-2248).*
Fu et al (EMBO Journal, 1996, 15:4392-4401).*
Yokota et al (Oncogene, 1988, 3:471-475).*
Bowie et al (Science, 1990, 247:1306-1310).*
Gussow et al (Methods in Enzymology, 1991, 203:99-121).*
Rudikoff et al., (PNAS, USA, 1982, 79:1979).*
Roitt et al, Immunology, 4t Ed., 1998, Mosby, London, p. 7.7-7.8).*
Holmes (Exp. Opin. Invest. Drugs, 2001, 10(3):511-519).*
Boehringer Mannheim Biochemicals, 1994 Catalog, p. 93.*
Oberg, A, et al, Limited value of preoperative serum analyses of matrix metalloproteinases (MMP-2, MMP-9) and tissue inhibitors . . . Anticancer Research, vol. 20, No. 2B, pp. 1085-1091 (abstract only, PubMed ID: 10810401).*
Tockman, MS, et al, 1992, Considerations in bringing a cancer biomarker to clinical application, Cancer Research, vol. 52, Suppl., pp. 2711s-2718s.*
Ward, AM, 1985, Tumour Markers, Developmental Oncology, vol. 21, pp. 90-106.*

(Continued)

Primary Examiner—Stephen L. Rawlings
(74) Attorney, Agent, or Firm—Foley & Lardner LLP (57) ABSTRACT

The invention is directed to a method of diagnosis of the existence and/or the pathological developmental stage and/or the grade of malignancy of carcinomas and/or sarcomas in mammals characterized by the preparation of a body sample of said mammals and the determination of the overexpression of the protein Nup88 in said sample and to antibodies suitable for performing the same.

9 Claims, 3 Drawing Sheets

OTHER PUBLICATIONS

Pohl, AL, et al, 1994, Neural network evaluation of multiple tumor markers for diagnosis of ovarian cancer (meeting abstract), Non-serial, 3rd International Conference of the Mediterranean Society of Tumor Marker Oncology, CANCERLIT Accession No. 95614997.*

Genesis Group Associates, Inc., 1997, New tests improve breast cancer prognosis, Genesis Report-Dx, vol. 6, No. 3, NLDB Accession No. 97:320100.*

Martinez et al., "The Nuclear Pore Complex Protein Nup88 Is Overexpressed In Tumor Cells", *Cancer Research*, National Library of Medicine, vol. 59:5408-5411, (1999).

Yasumoto et al., "Cancer-Specific Binding Of A Mouse MAb vs. Candida Krusei Cytochrome c: An antigen Recognized By A Cancer-Associated Human MAb HB4C5", *Hum. Antibod. Hybridomas*, Butterworth-Heinemann, vol. 4:186-189, (1993).

Schneider et al., "Cross-Reactivity Between *Candida albicans* And Human Ovarian Carcinoma As Revealed By Monoclonal antibodies PA10F and C6", *British Journal of Cancer*, Cancer Research Campaign, vol. 77(6):1015-1020, (1998).

van Deursen et al., "G2 Arrest And Impaired Nucleocytoplasmic Transport In Mouse Embryos Lacking The Proto-Oncogene CAN/Nup214", *The EMBO Journal*, Ocford University Press, vol. 15(20):5574-5583, (1996).

von Lindern et al., "The Translocation (6;9), Associated With A Specific Subtype Of Acute Myeloid Specific Leukemia, Results In The Fusion Of Two Genes, dek and can, And The Expression Of A Chimeric, Leukemia-dek-can mRNA", *Molecular And Cellular Biology*, American Society For Microbiology, vol. 12(4):1687-1697, (1992).

von Lindern et al., "can, A Putative Oncogene Associated With Myeloid Leukemogenesis, May Be Activated By Fusion Of Its 3' Half To Different Genes: Characterization of the Set Gene", American Society For Microbiology, vol. 12(8):3346-3355, (1992).

* cited by examiner

CANCER DIAGNOSIS BY THE MEASUREMENT OF NUP88 IN BODY SAMPLES

FIELD OF THE INVENTION

This invention relates to the field of cancer diagnosis. Particularly, this invention deals with the diagnosis of the existence and/or the pathological developmental stage and/or the grade of malignancy of carcinomas and/or sarcomas in mammals.

BACKGROUND ART

Mammalian cancer is the sixth most common cancer among women in the United States and constitutes the forth cause of death. Because of its asymptomatic early stage and the lack of an effective early-stage detection test, this cancer is the most lethal among all gynecological malignancies. Mammalian carcinogenesis involves multiple genetic changes, revealed as alterations in the expression of certain genes, particularly those related to cell cycle regulations, such as the tumor suppressor genes p53, p16, and BRCA, and the oncogenes AKT2, ras, and c-Myc. Understanding the mechanisms of these changes could lead to using the genes as markers for the detection of mammalian tumors at an early stage. All previously known markers for cancer have certain drawbacks. Some stain only a small subset of malignancies, others do not allow to discriminate between the different pathological developmental stages of the corresponding disease, while others also stain not malignant tumors.

In 1993, a monoclonal antibody directed against *candida krusei* cytochrome c was shown to react with a cytoplasmatic fraction protein of human ovarian carcinoma cell line (Yasumoto K., et al., 1993, Hum. Antib. Hybrid 4:186 ff.). Independently, it was reported that Nab C6, generated against *candida albicans* mannoproteins, reacted specifically with a 43 kDa-molecule from a human mammalian carcinoma cell line, but not with non-neoplastic counterpart cells (Schneider J., et al., 1996, Br. J. Cancer 77:1015–1020).

To sum up, it has been known in prior art that molecular antibody C6 crossreacts with some carcinoma cells but the target remained to be elusive. Accordingly, it is an object of the invention to provide for a new marker which is useful for cancer diagnosis.

SUMMARY OF THE INVENTION

In accordance with the purposes of this invention, as embodied and broadly described herein, this invention relates to a method of diagnosis of the existence and/or the pathological developmental stage and/or the grade of malignancy of carcinomas and/or sarcomas in mammals characterized by the preparation of a body sample of said mammals and the determination of the overexpression of the protein Nup88 in said sample. This invention further provides a diagnostic kit for carrying out the method of the invention and a monoclonal antibody.

DETAILED DESCRIPTION OF THE INVENTION

The invention is directed to a method of diagnosis of cancer, namely of all diseases belonging to the group of carcinomas and/or sarcomas of mammals. Carcinomas and/or sarcomas are epithelial tumors, epithelial tumors of the stomach, particularly infiltrating adenocarcinoma and in situ carcinoma, epithelial tumors of the colon, particularly infiltrating adenocarcinoma, in situ adenocarcinoma, villous adenoma, tubular adenoma, neuroendocrine carcinoma, epithelial tumors of the liver, particularly hepatocellular carcinoma, dysplastic nodules, epithelial tumors of the pancreas, particularly adenocarcinoma, neuroendocrine carcinoma, epithelial tumors of the breast, particularly infiltrating ductal carcinoma, infiltrating lobular carcinoma, in situ ductal carcinoma, in situ lobular carcinoma, fibroadenoma, fibrocystic disease, epithelial tumors of the lung, particularly squamous carcinoma, adenocarcinoma, broncholoalveolar carcinoma, large cell carcinoma, neuroendocrine carcinoma, carcinoid, hyperplastic bronchi, epithelial tumors of the ovary, particularly cystadenoma, benign teratoma, borderline serous carcinoma, borderline mucinous carcinoma, serous carcinoma, mucinous carcinoma, endometrioid carcinoma, clear cell carcinoma, epithelial tumors of the uterus, particularly endometrial carcinoma, endometrial hyperplasia, epithelial tumors of the prostate, particularly andenocarcinoma, PIN high grade, PIN low grade, benign glandula hyperplasia, epithelial tumors of the kidney, particularly clear cell carcinoma, epithelial tumors of the adrenal, particularly cortical adenoma, mesenchymal tumors, particularly fibrosarcoma, malignant fibrous histiocytoma, Kaposi sarcoma, dermatofibrosarcoma, protruberous giant cell tumor (benign), leiomyoma, atypical fibroxanthoma, angiolipoma, miscellaneous tumors, particularly large cell lymphomas, lymphoblastic lymphomas, Hodgin's disease, malignant mesothelioma, benign mesothelioma, glioblastoma multiforme, malignant melanoma.

The method of the invention is a diagnostic method for mammals, particularly those susceptible for veterinary or human medical care, preferably human beings. The method of the invention precludes the preparation of a body sample. The term body sample embraces but is not confined to blood, smears, sputum, urine, stool, liquor cerbrospinalis, bile, gastrointestinal secretion, lymphatic liquor and biopsies of organs to be tested. All these body samples have to undergo a preparation procedure as known in the art for the determination of the overexpression of proteins. For instance, biopsies are cut into slices which are investigated by means of histology. Another example would be the examination of blood by well known ELISA techniques (Enzyme Linked Immuno Sorbent Assay).

The method of the invention relies in the determination of the overexpression of the protein Nup88 in said body sample. Nup88 was recognized by the inventors as the mammalian molecule to which the monoclonal antibody C6, generated against *Candida albicans* mannoproteins crossreacted, when used to stain a tumor or mammalian carcinoma cell line (Nerea Martínez, Angel Alonso, María Dolores Moragues, José Potón, José Schneider, Cancer Research 59, 5408–5411, 1999, the disclosure of which is incorporated by reference). Nup88 (GeneBank Y08612) had been found to be associated with the central domain of CAN/Nup214, a nuclear pore complex component putatively implicated in the nuclear protein import, nuclear mRNA export, and the regulation of cell cycle (Van Deursen et al., Embo J. 15:5574–5583, 1996). Notably, the CAN/Nup214 protooncogene is involved in chromosomal rearrangements related to two variants of leukemia (von Lindern M., et al.: 1992, Mol. Cell. Biol. 12:1687–1697; von Lindern M., et al., 1992b, Mol. Cell. Biol. 12:3346–3355). The inventors showed by immunohistochemistry that a polyclonal antiserum directed to Nup88 recognized several human tumor cell lines as well as ovarian carcinomas in tissue sections; parallel results were obtained by immunoblot analysis (Martínez et al., 1999). Taken together, the results disclosed in Martínez et al., 1999 show that Nup88 is overexpressed in a series of tumor cell lines and in primary human ovarian tumors when compared with the corresponding tissue. Furthermore, now it has been found that overexpression of Nup88 in body samples is also indicative for the pathological developmental stage and/or the grade of malignancy of carcinomas and/or sarcomas. The term great of malignancy is to be understood according to Roche Lexikon Medizin, 4$^{th}$ edition, Urban and Fischer, München, p. 909, col. 1, p. 1057, col. 1. The diagnosis of the pathological developmental stage is defined according to Roche Lexikon Medizin, 4$^{th}$ edition, p. 1582.

The diagnostic method of the invention is based on the determination of the overexpression of protein Nup88 in a body sample. The term overexpression means in the context of the invention that more protein Nup88 can be found in the body sample than in healthy controlled tissue. A person skilled in the art is aware, that assessing overexpression may also include the cytological and histological localization of Nup88 in the body tissue to discriminate against artifacts and to improve the signal to noise ratio of the determination procedure. The apparent cytological localization of Nup88 may also be dependent on the determination method employed. For instance, immunofluorescence analysis showed that Nup88 is located mainly in the nuclear membrane and to a minor extent in the cytoplasma. In contrast, immunohistochemistry studies revealed a predominantly cytoplasmic accumulation of Nup88 in tumor cells (Martinez et al., 1999, p. 5410, col. 2, FIG. 4).

The determination of the overexpression of the protein Nup88 is preferably performed using a protein binding molecule binding to Nup88, that means that the overexpression status is determined by measuring the amount of the protein, e.g. by use of an ELISA system or a biosensor. Such protein binding molecules may be natural antibodies such as polyclonal or monoclonal antibodies or recombinant antibodies such as chimeric proteins that exhibit homology to antibodies of mammals. The generation of said chimeric proteins is well-known in the art and described for instance in EP-B-0 368 684 and Little M., Kipriyanov S. M., Le Gall F, Moldenhauer G. 2000, Immunol. Today: 21(8):364–70. These chimeric proteins can be prepared by amplification of the variable or hypervariable regions of anti-body genes of lymphocytes and the integration of these gene fragments in frame work vectors so as to produce all forms of recombinant antibodies. A particularly preferred protein binding molecule binding to Nup88 is the monoclonal antibody as deposited under the accesion number given by the international depositary authority DSM ACC2457 at DSMZ-Deutsche Sammung von Microorganismen und Zellkulturen GmbH, Mascheroder Weg 1b, D-38124 Braunschweig, Germany fulfilling the Budapest Treaty on the international recognition of the deposits of microorganisms for the purposes of patent procedure. This monoclonal antibody is particularly suited for the purposes of the invention because of its affinity and specificity. A further preferred protein binding molecule binding to Nup88 is a chimeric protein that exhibits homology to antibodies of mammals and which is further characterized in that at least one CDR region of said monoclonal antibody is virtually identical with the corresponding counterpart of 149/1/1 as deposited under DSM ACC 2457. The term CDR region is defined as known in the art, for instance in Little M., Kipriyanov S. M., Le Gall F. Moldenhauer G., Immunol. Today: 21(8):364–70, 2000 and in Suleyman S, Thompson K M, Mageed R A, Natvig J B, Scand J Immunol 2000 October;52(4):341–7 or in Takahashi M, Ueno A, Mihara H, Chemistry 2000 Sep. 1;6(17): 3196–203.

In a further embodiment of the invention, the overexpression of the protein Nup88 is determined by means of a nucleic acid binding molecule binding to the transcript of Nup88.

It is well-known in the art, that overexpression of proteins is usually accompanied by the up-regulation of the production of the corresponding transcripts. Accordingly, the overexpression of the proteins to be investigated can be shown indirectly by measuring the amount of the corresponding transcripts. This can be done by the use of nucleic acid binding molecules binding to the transcript of Nup88. Such nucleic acid binding molecules are, for instance, oligonucleotides such as DNA-heteromers or RNA-heteromers comprising 7 to 40 monomeric units. The determination of overexpression of the protein Nup88 using nucleic acid binding molecules binding to the transcript of Nup88 can be performed using methods well-known in the art like polymerase chain reaction (PCR), including RT-PCR, hybridization techniques, including northern blot hybridization and other techniques suitable for the measurement of mRNA transcripts.

A further embodiment of the present invention is a diagnostic kit for carrying out the method of the invention comprising a protein binding molecule binding to Nup88. Preferably, the diagnostic kit also contains the protein Nup88 or an antigenic part thereof for control reactions.

Yet, another diagnostic kit for carrying out the inventive method comprises a nucleic acid binding molecule binding to the transcript of Nup88.

Another embodiment of the invention is a monoclonal antibody as deposited under DSM ACC 2457.

The amino acid sequence (SEQ ID NO. 2) of accession number Y08612 is:

```
MAAAEGPVGDGELWQTWLPNHVVFLRLREGLKNQSPTEAEKPASSSLPSSPPPQLLTRNVVFGLGGELFLWDGED

SSFLVVRLRGPSGGGEEPALSQYQRLLCINPPLFEIYQVLLSPTQHHVALIGIKGLMVLELPKRWGKNSEFEGGK

STVNCSTTPVAERFFTSSTSLTLKHAAWYPSEILDPHVVLLTSDNVIRIYSLREPQTPTNVIILSEAEEESLVLN

KGRAYTASLGETAVAFDFGPLDAVPKTLFGQNGKDEVVAYPLYILYENGETFLTYISLLHSPGNIWKAVGSIAHA

SAAEDNYGYDACAVLCLPCVPNILVIATESGMLYHCVVLEGEEEDDHTSEKSWDSRIDLIPSLYVFECVELELAL

KLASGEDDPFDSDFSCPVKLHRDPKCPSRYHCTHEAGVHSVGLTWIHKLHKFLGSDEEDKDSLQELSTEQKCFVE

HILCTRPLPCRQPAPIRGFWIVPDILGPTMICITSTYECLIWPLLSTVHPASPPLLCTREDVEVAESSLRVLAET
```

-continued

PDSFEKHIRSILQRSVANPAFLKASEKDIAPPPEECLQLLSRATQVFREQYILKQDLAKEEIQRRVKLLCDQKKK

QLEDLSYCREERKSLREMAERLADKYEEAKEKQEDIMNRMKKLLHSFHSELPVLSDSERDMKKELQLIPDQLRHL

GNAIKQVTMKKDYQQQKMEKVLSLPKPTIILSAYQRKCIQSILKEEGEHIREMVKQINDIRNHVNF.

The nucleic acid sequence (SEQ ID NO. 1) encoding the protein of accession number Y08612 is:

```
   1 gataaaccca caagacacaa aacataccct tcgagcagtt gggccaagat ggcggccgcc
  61 gagggaccgg tgggcgacgg cgagctgtgg cagacctggc ttcctaacca cgtcgtgttc
 121 ttgcggctcc gggagggact gaaaaaccag agtccaaccg aagctgagaa accagcttct
 181 tcgtcgttgc cttcgtcgcc gccgccgcag ttgctgacga gaaacgtggt ctttggcctc
 241 ggcggagagc ttttcctgtg ggacggagaa gacagctcct tcttagtcgt tcgccttcgg
 301 ggccccagcg gcggcggcga agagcccgcc ctgtcccagt accagagatt gctttgcata
 361 aatccacccc tgtttgaaat ctatcaagtc ttgttaagcc aacacaaca tcatgtagca
 421 cttataggaa taaaaggact tatggtatta gaattaccta aaagatgggg gaagaattct
 481 gaatttgaag gtggaaaatc aacagtgaat tgtagtacca ctccagttgc ggagagattt
 541 ttcaccagtt ccacctctct gactctaaag catgctgcat ggtatccaag tgaaatcctg
 601 gatccccacg tagtgctgtt aacatcagac aacgtaatca gaatttactc tctacgtgag
 661 ccgcagacac ccactaacgt gataatactt tcagaagccg aagaggaaag tctagtactc
 721 aataaaggaa gggcgtatac cgcatctcta ggagagacag cagttgcatt tgactttggg
 781 ccattggacg cagtcccaaa gactctattt ggacaaaacg gcaaagatga agtagtggca
 841 tacccactgt acatcttata tgaaaatgga gagactttcc tgacatacat cagtctgtta
 901 cacagccctg gaaatatttg gaaagctgtt gggtccattg cccatgcatc tgcggctgaa
 961 gataactatg ttatgatgc gtgtgctgta ctctgcttac cctgtgtccc caatatctta
1021 gtgatcgcta ctgaatcagg aatgctgtat cactgtgtcg tgctagaagg ggaagaagaa
1081 gatgaccaca cgtcagaaaa gtcctgggat tccaggattg acctcattcc ttctctgtat
1141 gtgtttgaat gtgttgagtt ggagcttgct ttgaaactgg catctggaga ggatgaccct
1201 tttgattctg acttttcttg tccagtcaaa cttcatagag atcccaagtg tccttcaaga
1261 tatcactgta ctcatgaagc tggtgtacat agtgttgggc taacttggat tcataaactt
1321 cacaaatttc ttggatcaga tgaagaagat aaggatagtt tacaggaact ctctacagaa
1381 cagaaatgct tgttgaaca catcctttgt acgaggccat gccctgcag gcagccagct
1441 ccaattcgag gattttggat tgtacctgac attctgggac ccacgatgat ctgcatcacc
1501 agtacctatg aatgcctcat atggccgtta ttaagtacag tccatccagc gtctcctccc
1561 ctgctttgta ctcgagaaga tgttgaagtg gcagagtctt ccctccgtgt tctggctgaa
1621 acccagatt cctttgaaaa gcatattaga agcattttgc aacgtagtgt tgccaatcca
1681 gcattttga agcttctga aaaggacata gcccctcctc ctgaagaatg ccttcagctc
1741 ctcagcagag ccacccaggt gttcagagag cagtacattc tcaaacagga cttggcaaag
1801 gaggagattc agcggagggt caaattatta tgtgaccaaa aaagaaaca actagaagat
1861 ctcagttatt gtcgagaaga gaggaaaagt ctgcgggaaa tggctgagcg tttagctgac
1921 aaatatgagg aagctaaaga aaaacaagag gatatcatga acaggatgaa aaaactactt
1981 cacagttttc actctgagct cccagttctc tctgatagtg agcgagacat gaagaaagaa
```

-continued

```
2041 ttacagctga tacctgatca acttcgacat ttgggcaatg ccatcaaaca ggttactatg 2101 aaaaaggatt atcaacagca aaagatggag aaggtgttga gtcttccaaa acccaccatt 2161 attctcagtg cctaccagcg aaagtgcatt cagtccatcc tgaaagagga gggtgaacat 2221 ataagggaaa tggtgaagca aatcaatgat atccgcaatc atgtaaactt ctgacaccac 2281 caggagctga ctcacacctg aactgaacac cattgaaggc ttaaacccat attgtaaaac 2341 aggtagaatt atctaattta taaaaggtg ttttgatg.
```

BRIEF DESCRIPTION OF THE DRAWING

FIG. 1 (a) to (o) show immunohistochemical investigations of different tissues immunostained with polyclonal antiserum to Nup88.

Figure 1:
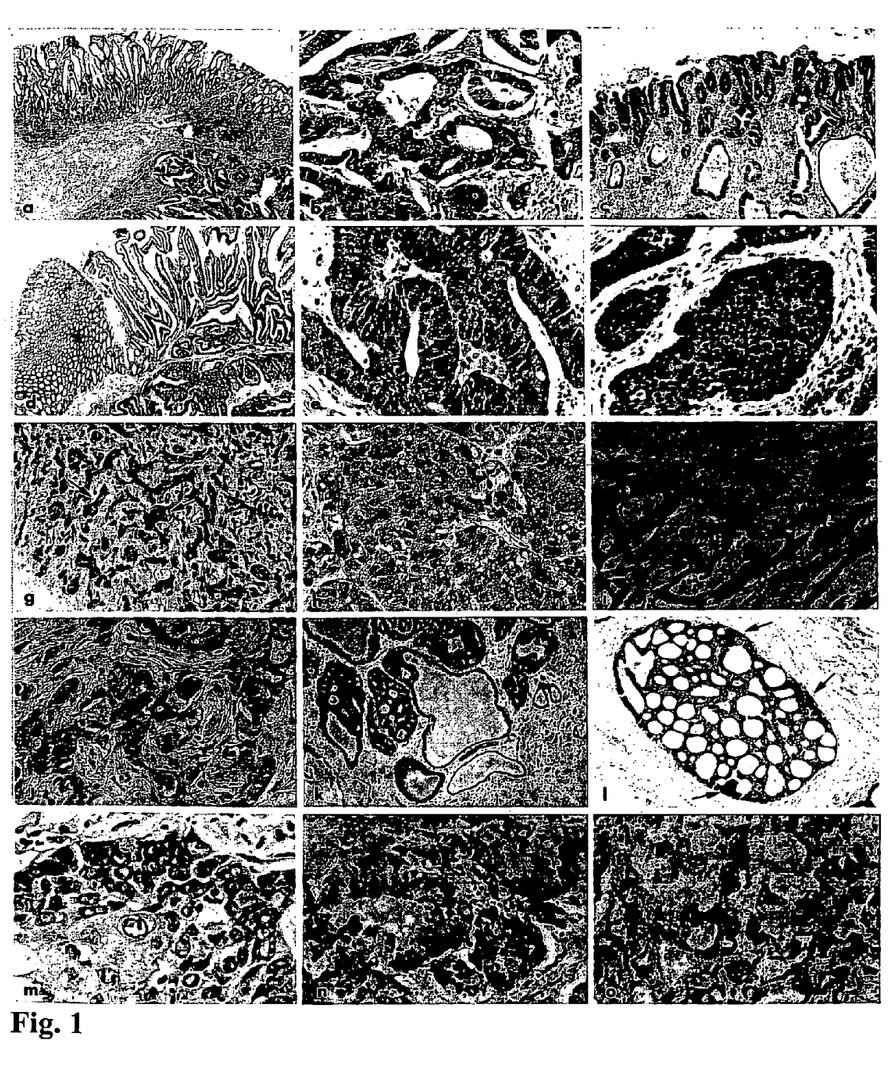

FIG. 1. (a) to (o) show immunohistochemical investigations of different tissues immunostained with polyclonal antiserum to Nup88 using DAB as a chromomogen (DAB: 3,3',4,4'-tertraaminobiphenyl).

1a) Stomach adenocarcinoma; the prominent, somewhat hyperplastic mucosa (upper field) is not reactive whereas the carcinoma invading the submucosa (lower right) is clearly stained. X 60

1b) Gastric adenocarcinoma; higher magnification of tumor in FIG. 1a. shows diffuse and intense immunostaining of carcinomatous glands. X480

1c) Somach with extensive intestinal metaplasia; a strongly and diffusely stained in situ carcinoma is evident. X 180

1d) Colon adenocarcinoma; the normal mucosa on the left part of the field is negative while the basal aspect of the glands of a villous adenoma are moderately reactive (arrow). The overt carcinoma invading the submucosa is richly stained. X120

1e) Colon adenocarcinoma; higher magnification of tumor in FIG. 1d shows diffuse, strong and granular reaction of malignant glands. X 620

1f) Colon, neuroendocrine carcinoma of colon. Note portions of characteristically organoid clusters diffusely reactive for Nup88. X 480

1g) Liver, cirrotic septum in the liver that included the carcinoma depicted in 1 h. Note reactivity in proliferating bile ductules (arrows) amidst non-reactive fibroconnective tissue. X180

1h) Liver, hepatocellular carcinoma; note strong, extensive and granular reaction. X620

1i) Pacreas, adeno carcinoma of pancreas showing strong Nup88 reaction of malignant glands. X420

1j) Breast, infiltrating ductal carcinoma of breast showing strongly Nup88 immunoreactive cell clusters. X 420

1k) Breast, fibrocystic changes of breast. Note negative hyperplastic and cystically dilated ducts. X120

1l) Breast, intraductal carcinoma of breast, cribriform variant. The reaction is diffuse but is best appreciated towards the periphery of the duct (arrows). X120

1m) Lung, well differentiated squamous carcinoma of lung; portion of neoplastic cluster showing strong staining particularly at the periphery of the aggregate; the central, more mature cells approaching pearl formation show but scanty reacting granules. X620

1n) Lung, moderately differentiated adenocarcinoma of lung; note strong and diffuse reaction. X480

1o) Bronchial carcinoid. Note moderately but diffusely reactive tumor ribbons and clusters amid the negative stroma. X 180

Figure 2:
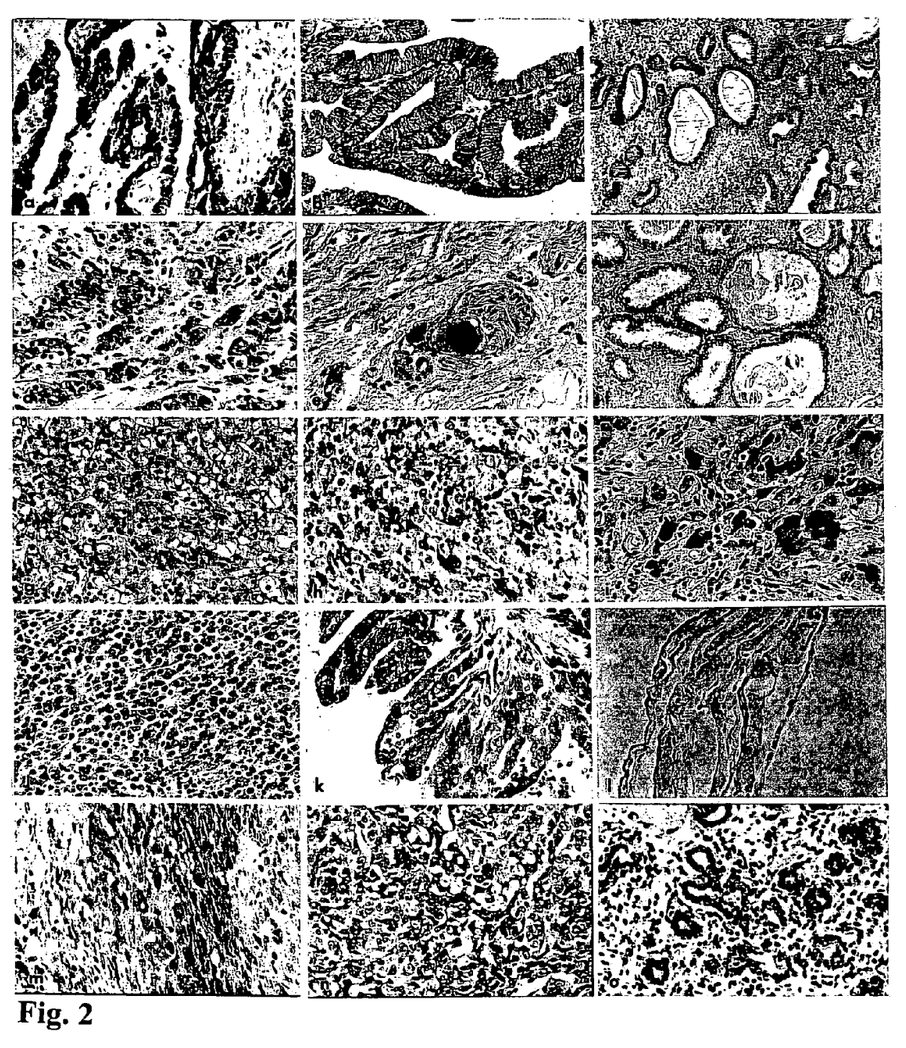
FIG. 2 shows immunohistochemical investigations of other tissues using the same antiserum.

FIG. 2.—the same antibody was used as described for FIG. 1. The chromogene used was DAB except for FIG. 2n for which we used alkaline phosphatase (red).

2a) Ovary, moderately differentiated ovarian serous cystadenocarcinoma; note rich and diffuse reaction of the neoplastic papillae. X480

2b) Endometrium, well differentiated endometrial adenocarcinoma showing strong and diffuse Nup88 reactivity. X480

2c) Endometrium, cystic endometrial hyperplasia; no reaction is evident. X 180

2d) Prostate, prostatic adenocarcinoma, (Gleason 4+5); strong reaction involving the majority of the malignant cells is seen. X 420

2e) Prostate, periphery of prostatic carcinoma shown in FIG. 2d. Small clusters of malignant cells are stained; note also the overwhelming reaction of neoplastic cells around and within a nerve. X 540

2f) Prostate showing variably hyperplastic and/or atrophic glands; no Nup 88 reaction is seen. X 180

2g) Kidney, renal cell carcinoma, clear cell type. A strong and extensive reaction is evident. X 480

2h) Soft tissue, malignant fibrous histiocytoma; a moderate but diffuse reaction involves most neoplastic cells. X480

Figure 3:
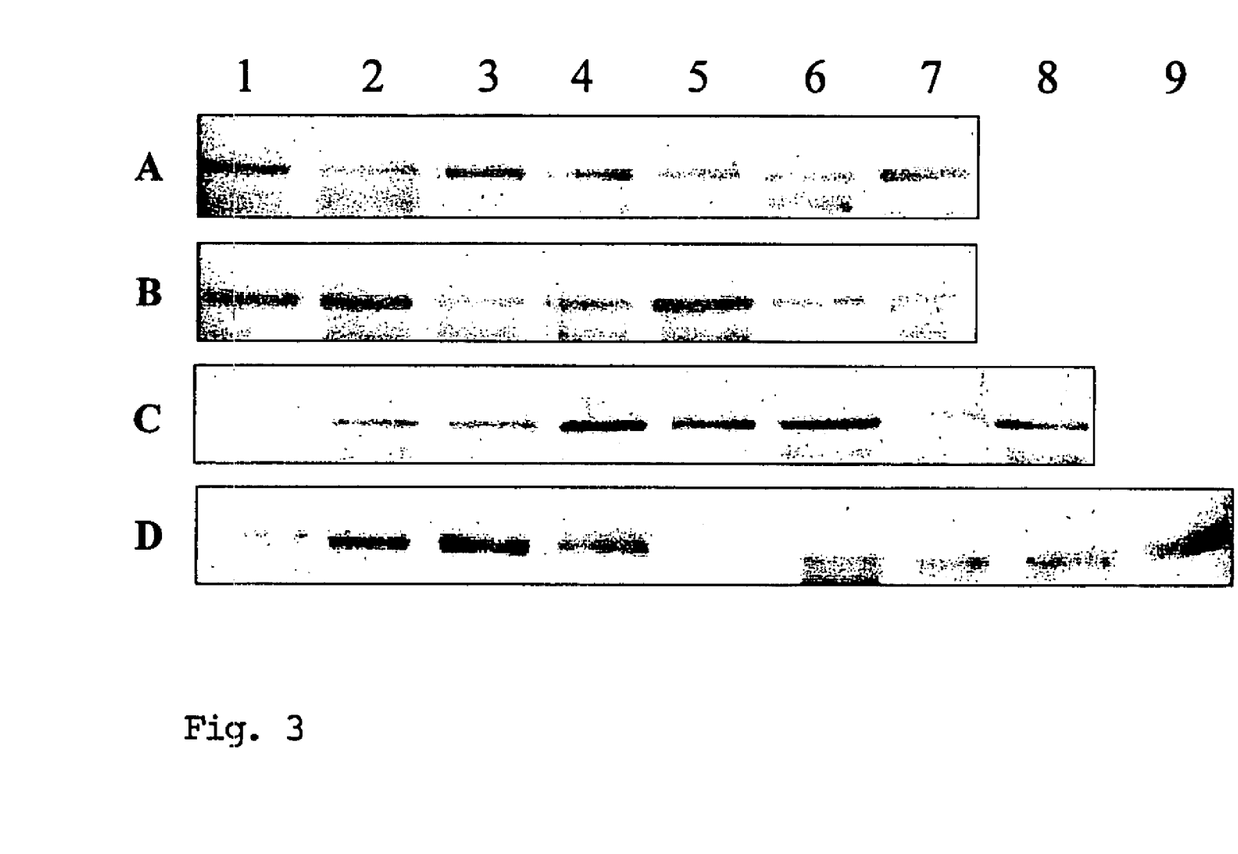
FIG. 3 shows an immunoblot analysis of Nup88 content in neoplastic, hyperplastic and normal tissues.

2i) Leiomyosarcoma metastatic to lung (see FIG. 3, immunoblot B5). Strong reactivity is evident particularly in the bizarre giant cells. X620

2j) Lymphe node, large cell lymphoblastic lymphoma diffusely reactive for Nup 88. X 160

2k) Pleura, malignant papillary mesothelioma richly and diffusely reactive for Nup88. X480

2l) Abdomen, benign cystic mesothelioma; no reaction is seen. X480

2m) Brain, glioblastoma multiforme; a rich and extensive reaction is evident. X480

2n) Skin, malignant melanoma using alkaline phosphatase as chromogen (red). A rich and diffuse reaction is noted. X480

2o) Fetal lung (20 weeks; 360g). A moderate but extensive reaction involves the primitive air spaces. X320

FIG. 3. Analysis of Nup88 content in tumors and normal tissues by immunoblotting. Total protein extracts of colon (A), lung (B), breast (C) and ovary (D) were prepared as described in Methods and probed with the polyclonal antiserum to Nup88.

A (colon): lanes 1, 2, 3, 4 and 5 represent adenocarcinomas; lane 6 is the negative control consisting of normal human lymphocytes while lane 7 is the positive control representing an ovarian carcinoma known to expressed aduntan Nup88 from previous studies.

B (lung): lane 1 represents a bronchial carcinoid depicted in FIG. 1o. Lanes 2 and 4 represent an adeno- and a squamous carcinoma respectively while lane 3 is a poorly differentiated squamous carcinoma treated with chemo- and radio-therapy prior to removal. The strongly reactive lane 5 represents a metastatic leiomyosarcoma depicted in FIG. 2i, lane 6 represents hyperplastic bronchi in the vicinity of but not involved by a carcinoma. Negative control, lane 7, as in A.

C (breast): lane 1 represents typical, benign, fibrocystic changes depicted in FIG. 1k. Lanes 2 and 3 represent fibroadenomas; lanes 4 and 5 represent infiltrating ductal carcinomas, while lane 6 is an infiltrating lobular carcinoma. Lane 7 is a normal (control) adult female breast while lane 8 is a known, positive ovarian carcinoma.

D (ovary): lane 1 represents a benign mucinous cystadenoma, lanes 2 and 3 represent papillary serous carcinomas, and lane 4 represents a metastasis from a gastric signet ring cell carcinoma. Lane 5 is a surprisingly low signal given by an endometrioid carcinoma, Lanes 6, 7 and 8 represent negative controls while lane 9 is the positive counterpart.

For further details see the following Example which illustrates the invention without limitation.

EXAMPLE

Material and Methods
  Samples
  Cases were selected on the basis of known diagnoses from the files of Rush-Presbyterian-Luke's Medical Center, Chicago, Ill. Most of these cases had been extensively studied and characterized in previous investigations. Autopsy samples from adult, and fetal tissues (stillborn) were obtained from RPSLMC. All surgical operations were performed with the appropriate, informed consents, and were based on well established therapeutic and/or diagnostic procedures. Autopsies were performed based on legal permits. The anonymity of the patients was duly protected in all cases. A total of 266 samples, includingg 230 surgical tissues, 20 adult autopsy samples and 16 fetal autopsy selected samples were studied. One or 2 paraffin blocks per case were chosen; diagnoses were confirmed on conventional hematoxylin and eosin stained sections by 2 independent observers (VEG and AO). All tissues had been fixed in formalin and conventionally processed. Sections for immunostaining were cut at 4 µm, set on coated slides and placed on a warmer at 6o° C. for 1 hour; subsequently, they were deparaffinized in xylene and graded alcohols. No pretreatment with microwaves or enzymes was applied prior to exposure to the primary antiserum. Immunostaing was accomplished by the avidin-biotin-peroxidase method as originally outlined by Hsu et al [Hsu S M, Raine L, Fanger H: Use of avidin-biotin-peroxidase complex (ABC) in immunoperoxidase techniques: a comparison between ABC and unlabelled antibody (PAP) procedures. J Histochem Cytochem 29: 577–580, 1981]; commercial reagents were used (Dako Corporation, Carpinteria, Calif.). Best results were obtained when the antiserum was applied overnight in a humid chamber at 4° C. at a concentration of 1/500; the diluent was that provided in a commercial kit (Ventana Medical Systems, Tucso, Ariz.). Binding sites were visualized with 3,3'diaminobenzidine (Aldrich Chemicals, Danvers, Mass.), in the case of melanocytic lesions, alkaline phosphatase (Dako) was used as chromogen. All sections were briefly counterstained with hematoxylin to improve nuclear visualization. As negative controls, slides were similarly processed but the primary antiserum was omitted. Staining intensity was rated as weak, moderate or strong; in heterogeneous cases, the rating of the predominant pattern was the one recorded. The extent of the reaction was defined by the percentage of reactive cells, and graded from negative (O) to 1+ to 5+ as previously described (Moll et al., 1987, Am J Pathol 127:288–304).

Immunoblots
  For immunoblot analysis, freshly obtained samples from surgical or autopsy material were placed in vials containing precooled isopentane, and snap frozen in liquid nitrogen. These samples were kept in a deep freezer at −80° C. until used. Tumors were homogenized in 2% SDS-0.14 M β-mercapthoethanol and then centrifuiged over a Qiashredder (Qiagen, Germany) columm to shear the DNA. The protein content of the samples was calculated with the DC protein assay system of Bio-Rad 80 µg of proteins were separated on 7% polyacrylamide gels. Proteins were electrotransferred to PVDF membranes, blocked with nonfat milk in PBS and incubated with our polyclonal antiserum at a dilution of 1:2000. After washing, the membranes were reacted with a POD-labelled goat-anti rabbit, washed again, and the reacting bands revealed with the ECL system of Amersham (Amersham, UK).

Results
  All malignant neoplasms stained convincingly; most reactions were moderate to strong, and 3+ to 5+ in extent; in the series studied, not a single malignant tumor could be said to be non-reactive. All in situ carcinomas were invariably positive as were, albeit less so, dysplastic lesions that did not reach the level of carcinoma in situ. Benign tumors showed variably extensive and generally weak immunoreactivity. Salient points are outlined in Table I.

Immunohistochemistry
  Epithelial Tumors
  Gastric carcinomas were extensively and strongly stained; the contrast was evident between the mostly negative overlying mucosa and the convincingly reactive invasive tumor (FIGS. 1a and 1b). Reactions were similar in tumors showing variably differentiated glands as in cases showing a linitis plastica pattern of diffusely invasive single cells. One case included intestinal metaplasia with some dilated glands as well as carcinoma in-situ and infiltrating carcinoma; notably the metaplastic and dilated glands were negative while the in-situ carcinoma was strongly stained (FIG. 1c). The immunostaining pattern was characteristically punctiform; the granules were rather large as compared with the delicate dots seen in synaptophysin reactions (Wiedenmann et al., 1986, Proc. Natl. Acad Sci USA 83:3500–3504; Gould et al., 1987, Am. J. Pathol 126:243–257). Focally, a perinuclear localization was evident but predominantly the distribution was diffuse through the cytoplasm (see below); the cell membrane was not reactive. This pattern was consistently repeated in all samples studied.

Colonic adenocarcinomas were strongly and diffusely reactive. Blocks of several cases included normal colonic mucosa, polyps with variable degrees of dysplasia and infiltrating carcinoma; in these cases, the normal mucosa was for the most part negative, the polyps showed variable degrees and extent of staining generally parallelling the degree of dysplasia while the infiltrating carcinomas were invariably strongly and extensively stained (FIGS. 1*d* and 1*e*). Two carcinomas of mixed exocrine/neuroendocrine phenotypes and 2 pure neuroendocrine carcinomas were similarly stained (FIG. 1*f*). In polyps not associated with carcinoma, villous adenomas stained stronger that their blander, tubular counterparts; foci of intramucosal carcinoma in the former reacted even more convincingly. Hepatocellular carcinomas were strongly stained. One of these developed in the background of a severe cirrhosis; in this case, the proliferating bile ducts noted in the cirrhotic septa showed sporadic, moderately reactive cells (FIG. 1*g*) while the adjacent carcinoma was diffusely and intensely reactive (FIG. 1*h*). Seven pancreatic adenocarcinomas of variable degrees of differentiation showed moderate to strong, and consistently diffuse reactions (FIG. 1*i*); two neuroendocrine carcinomas were similarly stained. Regardless of tumor phenotype, non-neoplastic exocrine and neuroendocrine cells in the vicinity of the tumors or entrapped within them were occasionally and focally reactive.

All infiltrating breast carcinomas of ductal (FIG. 1*j*) or lobular types reacted convincingly while non-neoplastic ducts nearby or trapped within them did not stain. Mucinous (colloid) carcinomas showed strong staining of the scanty malignant cells whereas the dominant mucous pools did not react. In several carcinomas, we noted the strongest staining in the peripheral, invasive edge of the tumors. Fibrocystic areas including cyst formation, ductal hyperplasia, adenosis, papillomas and apocrine metaplasia in the vicity of carcinomas showed focal, weak to moderate staining while similar areas not associated with carcinoma ranged from minimally reactive to entirely negative (FIG. 1*k*). Regardless of the presence of a synchronous carcinoma, significantly atypical ducts and ductal carcinomas in situ of all types reacted convincingly (FIG. 1*l*).

Pulmonary squamous, adeno-, bronchioloalveolar, large cell and neuroendocrine carcinomas of all types stained richly and extensively (FIG. 1*m* and 1*n*); notably, hyperplastic but non-neoplastic bronchi in the vicinity of and within tumors were often strongly stained. All bronchial carcinoids studied stained diffusely; the intensity of the reactions varied; moderate staining predominated but focally strong staining was occasionally noted (FIG. 1*o*).

Ovarian carcinomas including serous, mucinous, clear cell and endometrioid types were convincingly stained; borderline tumors stained moderately while their invasive (FIG. 2*a*), and particularly their high grade counterparts were intensely reactive. Benign cystadenomas and cystadenofibromas showed uneven, weak to moderate reactions. In a benign teratoma, cartilagenous cells, the basal cells of skin adnexa and respiratoty-type epithelium showed moderate reactions. Endometrial carcinomas including endometrioid, clear cell and serous variants reacted strongly and extensively. Several of these cases were associated with endometrial hyperplasia; interestingly, while the carcinomas stained strongly, the bland variants of hyperplasia did not (FIGS. 2*b* and 2*c*). Also interesting was that the superficial, luminal aspect of several tumors stained less intensely than the deeper, invasive portion.

All prostatic carcinomas reacted strongly and diffusely irrespective of degree of differentiation (FIG. 2*d*) while non-neoplastic ducts and acini entrapped within them stained weakly and sporadically or not at all. In the case of poorly differentiated and hypernephroid carcinomas, single reactive cells were readily detected as were minute clusters around or within nerves (FIG. 2*e*). Several carcinomas included convincing foci of PIN (prostatic intraepithelial neoplasia) which were convincingly stained. Benign, hyperplastic and atrophic glands were either negative (FIG. 2*f*) or showed rare, positive cells, most often in the vicinity of carcinoma. All renal carcinomas were of clear cell type and all reacted strongly (FIG. 2*g*); some reactive renal tubules in the vicinity stained as well. Adrenocortical adenomas showed weak but fairly extensive reactions.

Mesenchymal Tumors

Fibrosarcomas, malignant fibrous histiocytomas (FIG. 2*h*), and Kaposi sarcomas reacted strongly and extensively; a single leiomyosarcoma reacted strongly in both primary and metastatic sites (FIG. 2*i*). Dermatofibrosarcoma protruberans, infantile fibrosarcomas, benign giant cell tumors, atypical fibroxanthomas and angiolipomas showed decreasingly extensive and moderate to weak reactions. Two (uterine) leiomyomas stained rather extensively but weakly.

Miscellaneous Tumors and Fetal Tissues

Diffuse large cell lymphomas stained strongly and diffusely as did a lymphoblastic lymphoma (FIG. 2*j*). In several cases of Hodgkin's disease, the Reed-Stemberg and the lacunar cells stained convincingly whereas the associated non-neoplastic leukocytes did not. Malignant mesotheliomas stained strongly (FIG. 2*k*); similar reactions were noted in epithelioid, sarcomatoid and biphasic variants. In contrast, samples from benign cystic mesotheliomas (multiple peritoneal inclusion cysts) were consistently negative (FIG. 2*l*). High-grade glioblastomas stained strongly and extensively (FIG. 2*m*). In-situ malignant melanomas showed convincing staining of the dysplastic melanocytes at the base of the epidermis, and of single cells migrating upwards in the epidermis. In invasive melanomas of various sites, reactions were diffuse and strong, and the coexistence of melanin and immunoreactive granules was clearly detectable in numerous cells (FIG. 2*n*); reactions were indistinguishable in epithelioid aggregates and in sarcomatoid foci.

Fetal samples were included in the study based primarily on the state of tissue preservation. Reactions were particularly convincing in developing bronchi and primitive air spaces (FIG. 2*o*) as well as in the crypts of the colonic mucosa.

Immunoblots

The results of these experiments are shown in FIG. 3. In all samples of malignant tumors analysed, a clear increase in the amount of Nup88 was observed. All colon carcinomas showed reactive bands that were far stronger than the corresponding controls (A-6); the comparatively weak band noted in A-2 may reflect the tumor's extensive necrosis. In the case of lung tumors, the respectable band seen in the bronchial carcinoid (B-1) corresponds in fact to a rather intensely reactive tumor (FIG. 1*o*). Notice also the strong B-2 and B-4 bands (carcinomas) and compare with the relatively meager B-3 lane that represents a carcinoma treated with radiation and chemotherapy resulting in extensive tumor necrosis prior to surgical removal. The strong B-5 band corresponds to a leiomyosarcoma metastatic to the lung (FIG. 2*i*), and the weak but distinct B-6 corresponds to bronchi showing epithelial hyperplasia and metaplastic changes in the vicinity of a carcinoma. The contrast between benign and malignant proliferations in the same organ is well exemplified in the series of breast lesions wherein all carcinomas (C-4, C-5 and C-6) show prominent bands while fibroadenomas (C-2 and C-3) and one bland variant of fibrocystic disease (C-1, corresponds to FIG. 1*k*) show delicate bands, and the sample of normal breast is virtually negative (C-7). In the case of the ovary, the meager band noted in D-1 (benign cystadenoma) offers a stark contrast with the broad bands seen in the carcinomas (D2, D3 and D4). Other than problems related to sampling, we cannot explain the weak band of the endometrioid carcinoma (D5) that by immunohistochemistry was moderately but convincingly decorated.

Densitometric quantification of the blots showed an increased expression in carcinomas between 1,5 and 5 times as compared with normal controls. However, it should be considered that these figures most probably represent a significant underestimation given that they do not take into account the considerable amounts of stroma that many of these tumors had. More detailed quantitative analyses should be performed based on larger pools of samples, and subsequent to appropriate microdisection.

Discussion

Our immunohistochemical results strongly reinforced by data from immunoblots of selected samples point to Nup88 as a molecule of exceedingly wide distribution that is consistently overexpressed in a broad spectrum of carcinomas, as well as in malignant mesotheliomas, many sarcomas, melanomas, gliomas and some lymphorecticular tumors. Nup88 expression was similarly enhanced in severe dysplasias and in situ carcinomas of organs such as colon, stomach, breast and prostate. We also showed distinct Nup88 enhancement during fetal development in sites including primitive pulmonary air spaces and colonic crypts. Focal expression was also noted in proliferative-reparative tissues in the vicinity of tumors, e.g., hyperplastic bronchial mucosa. Conversely, Nup88 was either sporadic or not detectable in most benign tumors and hyperplasias. In normal adult tissues, Nup88 was noted sporadically in sites such as colonic crypts, bronchial mucosa and fallopian tubes.

With regard to epithelial cancers, Nup88 enhancement was seen not only across a broad spectrum of sites but through all major differentiation lines. Thus, lung carcinomas with squamous, glandular and neuroendocrine features were strongly positive. In the GI tract and pancreas adeno- and neuroendocrine carcinomas were similarly positive, while in the ovary, serous, mucinous, endometrioid and clear cell carcinomas reacted as well. In addition, as noted earlier (Martinez et al, 1999), we also found that in sites such as the ovary, high grade carcinomas seemed to react more vigorously than their low grade or borderline counterparts. Furthermore, in some breast and endometrial carcinomas, we noted that the invasive periphery of the tumors stained more strongly than the center. The small number of cases studied to-date do not permit definite conclusions; yet, the potential significance of these observations merits re-exploration not only in the ovary but in other tumor systems. Also, interesting is that Nup88 overexpression seems to be independent of site of origin or presumed histogenesis as it was found in carcinomas from diverse organs derived from all embryonal layers.

Nup88 enhancement was clearly evident in severe epithelial dysplasias and in situ carcinomas of the colon, stomach, breast and prostate. This overexpression was evident irrespective of the presence or absence of an overt, synchronous cancer. Conversely, benign variants of conditions such as fibrocystic disease of the breast, endometrial hyperplasia, tubular adenomas of the colon and prostatic hyperplasia showed for the most part no significant Nup88 enhancement. Similar contrasts were noted in mesenchymal and other miscellaneous malignancies, i.e., strong reactions in a leiomyosarcoma and in malignant mesotheliomas contrasting with weak or absent staining in their benign counterparts. Notably, certain active reparative lesions, e.g., bile duct proliferation in cirrhosis associated with carcinoma, and proliferating renal tubules in the vicinity of renal carcinomas associated with pyelonephritis showed focal but convincing Nup88 overexpression. Interestingly, such areas are known to undergo active remodelling as reflected by the enhancement of pertinent matrix molecules, e.g. tenascin, cellular fibronectins (Howeedy et al., 1990, Lab Invest 63:798–806; Gould et al, 1992, Lab Invest 67:71–79). These findings indicate that enhanced Nup88 reflects a certain selective cellular proliferation that is most often but not exclusively associated with the malignant or premalignant phenotypes.

Some of the above findings of Nup88 overexpression in malignancy coupled with its detection in some fetal tissues suggest some parallels between it and a number of oncodevelopmental marker molecules including CEA and related substances. However, the latter molecules are for the most part membrane-associated glycoproteins known to or suspected of subserving cell—cell adhesive functions (for overview and ref's see Koukoulis et al., 1998, Hum Pathol 30:1273–1275; Gould and Gould, 1999, Hum Pathol 30:1273–1275). In addition, they are selectively expressed in some epithelia but are virtually absent in others, and in non-epithelial tissues. Moreover, the characteristically punctiform perinuclear and cytoplasmic localization of Nup88 differs substantially from that of the above molecules. These observations added to those that Nup88 is also significantly enhanced in malignancies as diverse as carcinomas, some sarcomas and lymphomas, mesotheliomas, melanomas and gliomas point to significant differences between Nup88 and on-codevelopmental markers currently used.

A consistent finding in the present study was the predominantly cytoplasmic location of the overexpressed protein in the involved cells. Our previous studies on several cell lines showed that most of the protein was located at the nuclear membrane with comparatively small amounts in the cytoplasm. Noteworthy, in many neoplastic and some non-neoplastic cells is the presence of aggregates of annulate lamellae (Ghadially F N: Ultrastructural pathology of the cell and matrix. 1997, $4^{th}$ ed, Butterworth-Heinmann, Boston, USA); and, these structures are thought derive from nuclear membranes (Kessel, 1983, Intertl Rev Cytol 82:181–305), and show features of the latter e.g. components of nuclear pore complexes including nucleoporins as described in *Xenopus* oocytes (Cordes et al, 1995, Eur J Cell Biol 68:250–255), and rat cells wherein they were visualized as cytoplasmic dots (Ewald et al., 1996, J Cell Sci, 109, 1813–24). Therefore, we speculate that the conspicuous cytoplasmic granules we found might reflect increased numbers of annullate lamellae. In this context, it merits mentioning that other oncoproteins may also be aberrantly located, e.g., the known nuclear-cytoplasmic mislocation of the BRCA 1 gene product in breast carcinomas (Chen et al., J Biol Chem 271:32863–8).

The polyclonal antiserum applied in these experiments allowed us to recognize clearly and consistently a Mr 88,000 band in immunoblot experiments. In addition, other weakly, reactive bands were at times detectable. The precise nature of these additional reactive bands remains unclear, but it should be stated that our antibody reacts strongly with the GST-Nup88 fusion proteins used for the immunization of the rabbits (Martinez et al., 1999). Also significant is that we cannot as yet state whether the aforementioned bands of lower molecular weight reflect degradation products of a single molecule or additional, separate proteins that share a similar or a common epitope. The eventual identification of the epitope recognized by our antibody should help elucidate the fragment of the protein recognized by it. In our current data, some questions may be said to persist as to whether the material recognized by our antiserum corresponds in fact to Nup88. Significantly, in carcinomas of various sites, and in one sarcoma, strong and extensive immunostaining of tissue sections was paralleled by similarly strong Mw 88,000 reactive bands in western blots of the same samples; conversely, in samples of hyperplasias, benign tumors, and normal tissues, scanty, weak or absent tissue staining was reflected by weakly reactive bands in the corresponding immunoblots. Moreover, no differences in intensity were noted in the additional, reacting bands found in tumors as well as controls thus reinforcing the notion that our antiserum is specific for Nup88. These data strongly suggest that the molecule in question corresponds indeed to Nup88. In vertebrate cells, the nuclear pore complex (NPC) (for recent overview and ref's see Allen et al., 2000, J Cell Sci 113: 1651–1659; Blobel and Wozniak, 2000, Nature 403:835–836) is a large macromolecular aggregate with an estimated molecular mass of 125 MDa (Reichelt et al., 1990, J Cell Biol 110:883–894); it includes 50– 100 proteins termed nucleoporins (Fountura at al., 1999, J Cell Biol 144: 1097–1112). Conversely, in yeast, NPC are smaller, have a molecular mass in the range of 66 MDa, and may include 30–40 nucleoporins (Rout and Blobel, 1993, J Cell Biol 123, 771–783). Among the known nucleoporins, the rather recently characterized Nup 88 in its dynamic subcomplex association with the oncogenic nucleoporin CAN/Nup214 seems to play essential roles; depletion of the complex results in defective import-export processes, and eventual cell cycle arrest (Fornerod et al., 1997, EMBO J. 16:807–816); and, in overexpressing cells, it appears that CAN/Nup214 and one of its interacting proteins, i.e. Nup88, may function on both faces of the NPC (Boer et al., Exp. Cell Res 232, 182–185). Notably, preliminary experiments in our laboratory showed no increased expression of CAN/Nup214 in our tumor samples thus suggesting an uncoupling of the former from Nup88 at least in some instances. Interesting in this context is the fact, that the Nup98 gene seems to be involved in therapy-related leukemias by a translocation producing fusion proteins that may act as transcription factors modulating expression of other genes (Nishiyama at al., 1999, Genes Chromosomes Cancer 3, 215–220).

We can only speculate about the possible role (s) of Nup88 in malignant cells. A possible explanation is that its overexpression is simply the result of increased nucleocytoplasmic transport required to meet the growing demand of proteins by transformed cells. Increased traffic is indeed known to occur; in this context, it merits mention that the diameter of the pore channel in transformed mammalian cells is known to be increased (Feldherr and Aikin, 1995 Membr Prot Trans 2:237–259). An alternative explanation is that Nup88 may play a role in the formation and maintenance of anullate lamellae as outlined above; but while this might explain their presence it would not clarify their function.

Our findings suggest that this molecule may be a potentially significant marker given its dramatic overexpression in a broad spectrum of malignant tumors of literally all denominations. If these results were confirmed, Nup88 might be said to approach an ideal, generic marker of transformation readily demonstrable on conventional tissue sections, and possibly in cytologic samples.

TABLE I

Nup88 Immunoreactivity of Tumors & Related Conditions

| Site and Diagnosis | # of Cases & Reaction | [1]Extent of Reaction | [2]Intensity of Reaction |
|---|---|---|---|
| EPITHELIAL TUMORS | | | |
| STOMACH | | | |
| Infiltrating adenocarcinoma | 11/11 | 3+/5+ | m/s |
| In situ carcinoma | 2/2 | 3+/4+ | m/s |
| COLON | | | |
| Infiltrating adenocarcinoma | 12/12 | 3+/5+ | m/s |
| In situ adenocarcinoma | 3/3 | 2+/4+ | m |
| Villous adenoma | 3/3 | 2+/3+ | m |
| Tubular adenoma | 5/5 | 2+/3+ | w/m |
| Neuroendocrine carcinoma | 2/2 | 3+/4+ | m/s |
| LIVER | | | |
| Hepatocellular carcinoma | 4/2 | 3+/5+ | m/s |
| Dysplastic nodules | 2/2 | 2+/3+ | w |
| PANCREAS | | | |
| Adenocarcinoma | 7/7 | 3+/4+ | m/s |
| Neuroendocrine carcinoma | 3/3 | 3+/4+ | m/s |
| BREAST | | | |
| Infiltration ductal carcinoma | 14/14 | 3+/5 | m/s |
| Infiltrating lobular carcinoma | 12/12 | 3+/5+ | m/s |
| In situ ductal carcinoma | 16/16 | 3+/4+ | m |
| In situ lobular carcinoma | 5/5 | 3+ | m |
| Fibroadenomas | 2/5 | 1+ | w |
| Fibrocystic disease | 16/28 | 1+/3+ | w/m |
| LUNG | | | |
| Squamous carcinoma | 8/8 | 3+/5+ | m/s |
| Adenocarcinoma | 12/12 | 3+/5+ | m/s |
| Broncholoalveolar carcinoma | 2/2 | 3+/4+ | m |
| Large cell carcinoma | 3/3 | 3+/5+ | m/s |
| Neuroendocrine carcinoma | 14/14 | 3+/5+ | m/s |
| Carcinoid | 9/9 | 2+/4+ | m |
| Hyperplastic bronchi | 3/3 | 2+/3+ | w/m |
| OVARY | | | |
| Cystadenoma | 2/3 | 2+ | w/m |
| Benign teratoma | 1/1 | 2+ | w/m |
| Borderline serous carcinoma | 2/2 | 2+/3+ | m |
| Borderline mucinous carcinoma | 2/2 | 2+/3+ | m |
| Serons carcinoma | 6/6 | 3+/5+ | m/s |
| Mucinous carcinoma | 4/4 | 3+/5+ | m/s |
| Endometrioid carcinoma | 1/1 | 4+ | m/s |
| Clear cell carcinoma | 2/2 | 3+/5 | m/s |
| UTERUS | | | |
| Endometrial carcinoma | 12/12 | 3+/5+ | m/s |
| Endometrial hyperplasia | 4/10 | 0/2+ | w |
| PROSTATE | | | |
| Adenocarcinoma | 11/11 | 3+/5+ | m/s |
| PIN, high grade | 6/6 | 2+3+ | m/s |
| PIN, low grade | 2/4 | 1+/2+ | w/m |
| Benign glandular hyperplasia | 2/6 | (+)/2+ | w/m |
| KIDNEY | | | |
| Clear cell carcinoma | 4/4 | 3+/5+ | m/s |
| ADRENAL | | | |
| Cortical adenoma | 2/2 | 2+/3+ | w |
| MESENCHYMAL TUMORS | | | |
| Fibrosarcoma | 5/5 | 3+/4+ | m |
| Malignaut fibrons histiocytoma | 7/7 | 3+/4+ | w/m |
| Kaposi sarcoma | 2/2 | 3+/4+ | m |
| Dermatofibrosarcoma Protruberous | 5/5 | 3+/4+ | m |
| Giant cell tumor, benign | 0/2 | 0 | — |
| Leiomyoma | 2/2 | 3+/4+ | w |

TABLE I-continued

Nup88 Immunoreactivity of Tumors & Related Conditions

| Site and Diagnosis | # of Cases & Reaction | [1]Extent of Reaction | [2]Intensity of Reaction |
|---|---|---|---|
| Atypical fibroxanthoma | 2/2 | 2+/3+ | w |
| Angiolipoma | 1/2 | (+) | w |
| MISCELLANEOUS TUMORS | | | |
| Large cell lymphoma | 3/3 | 3+/4+ | m |
| Lymphoblastic lymphoma | 1/1 | 3+/4+ | m |
| Hodgkin's disease | 4/4 | 2+/3+ | m |
| Malignant mesothelioma | 5/5 | 3+/5+ | m/s |
| Benign mesothelioma | 0/2 | 0 | — |
| Glioblastoma multiforme | 4/4 | 3+/5+ | |
| Malignant melanoma | | | m/s |
| Infiltrating | 4/4 | 3+/5+ | m/s |
| In situ | 2/2 | 3+/4+ | m/s |

(+): <1% positive cells
1+: 1–5% positive cells
2+: 6–15% positive cells
2+: 16–50% positive cells
4+: 51–95% positive cells
5+: 95% positive cells
w: weak
m: medium
s: strong

The invention claimed is:

1. A monoclonal antibody as deposited under DSM ACC 2457.

2. A method for identifying the presence of a malignant cancer cell comprising: (a) providing a tissue biopsy sample; and (b) determining the level of expression in the tissue biopsy sample of the protein consisting of the amino acid sequence (SEQ ID NO: 2):

MAAAEGPVGDGELWQTWLPNHVVFLRLREGLKNQSPTEAEKPASSSL

PSSPPPQLLTRNVVFGLGGELFLWDGEDSSFLVVRLRGPSGGGEEPAL

SQYQRLLCINPPLFEIYQVLLSPTQHHVALIGIKGLMVLELPKRWGKNSE

FEGGKSTVNCSTTPVAERFFTSSTSLTLKHAAWYPSEILDPHVVLLTSD

NVIRIYSLREPQTPTNVIILSEAEEESLVLNKGRAYTASLGETAVAFDFG

PLDAVPKTLFGQNGKDEVVAYPLYILYENGETFLTYISLLHSPGNIWKAV

GSIAHASAAEDNYGYDACAVLCLPCVPNILVIATESGMLYHCVVLEGEEE

DDHTSEKSWDSRIDLIPSLYVFECVELELALKLASGEDDPFDSDFSCPVK

LHRDPKCPSRYHCTHEAGVHSVGLTWIHKLHKFLGSDEEDKDSLQELST

EQKCFVEHILCTRPLPCRQPAPIRGFWIVPDILGPTMICITSTYECLIWP

LLSTVHPASPPLLCTREDVEVAESSLRVLAETPDSFEKHIRSILQRSVAN

PAFLKASEKDIAPPPEECLQLLSRATQVFREQYILKQDLAKEEIQRRVKL

LCDQKKKQLEDLSYCREERKSLREMAERLADKYEEAKEKQEDIMNRMKKL

LHSFHSELPVLSDSERDMKKELQLIPDQLRHLGNAIKQVTMKKDYQQQK

MEKVLSLPKPTIILSAYQRKCIQSILKEEGEHIREMVKQINDIRNHVNF, by contacting the sample with the monoclonal antibody deposited under DSM ACC 2457, which binds to the protein, wherein the tissue biopsy sample comprises a malignant cancer cell if the expression level of the protein is greater than the expression level of that protein in healthy or normal control tissue.

3. The method according to claim 2, wherein said malignant cancer cell is a cell in an epithelial or mesenchymal tumor.

4. The method according to claim 2, wherein said tissue biopsy sample is from a mammal.

5. The method according to claim 4, wherein said mammal is a human.

6. A kit for diagnosing the presence of a malignant cancer cell, comprising the monoclonal antibody deposited under DSM ACC 2457, which binds to the protein consisting of the amino acid sequence (SEQ ID NO: 2):

```
MAAAEGPVGDGELWQTWLPNHVVFLRLREGLKNQSPTEAEKPASSSLPSSPPPQLLT
RNVVFGLGGELFLWDGEDSSFLVVRLRGPSGGGEEPALSQYQRLLCINPPLFEIYQVLLSPTQ
HHVALIGIKGLMVLELPKRWGKNSEFEGGKSTVNCSTTPVAERFFTSSTSLTLKHAAWYPSEI
LDPHVVLLTSDNVIRIYSLREPQTPTNVIILSEAEEESLVLNKGRAYTASLGETAVAFDFGPLD
AVPKTLFGQNGKDEVVAYPLYILYENGETFLTYISLLHSPGNIWKAVGSIAHASAAEDNYGY
DACAVLCLPCVPNILVIATESGMLYHCVVLEGEEEDDHTSEKSWDSRIDLIPSLYVFECVELE
LALKLASGEDDPFDSDFSCPVKLHRDPKCPSRYHCTHEAGVHSVGLTWIHKLHKFLGSDEED
KDSLQELSTEQKCFVEHILCTRPLPCRQPAPIRGFWIVPDILGPTMICITSTYECLIWPLLSTVHP
ASPPLLCTREDVEVAESSLRVLAETPDSFEKHIRSILQRSVANPAFLKASEKDIAPPPEECLQLL
SRATQVFREQYILKQDLAKEEIQRRVKLLCDQKKKQLEDLSYCREERKSLREMAERLADKY
EEAKEKQEDIMNRMKKLLHSFHSELPVLSDSERDMKKELQLIPDQLRHLGNAIKQVTMKKD
YQQQKMEKVLSLPKPTIILSAYQRKCIQSILKEEGEHIREMVKQINDIRNHVNF.
```

7. The kit of claim 6, further comprising a nucleic acid that binds to a nucleic acid transcript that encodes the protein consisting of the amino acid sequence (SEQ ID NO: 2):

```
MAAAEGPVGDGELWQTWLPNHVVFLRLREGLKNQSPTEAEKPASSSLPSSPPPQLLT
RNVVFGLGGELFLWDGEDSSFLVVRLRGPSGGGEEPALSQYQRLLCINPPLFEIYQVLLSPTQ
HHVALIGIKGLMVLELPKRWGKNSEFEGGKSTVNCSTTPVAERFFTSSTSLTLKHAAWYPSEI
LDPHVVLLTSDNVIRIYSLREPQTPTNVIILSEAEEESLVLNKGRAYTASLGETAVAFDFGPLD
AVPKTLFGQNGKDEVVAYPLYILYENGETFLTYISLLHSPGNIWKAVGSIAHASAAEDNYGY
DACAVLCLPCVPNILVIATESGMLYHCVVLEGEEEDDHTSEKSWDSRIDLIPSLYVFECVELE
LALKLASGEDDPFDSDFSCPVKLHRDPKCPSRYHCTHEAGVHSVGLTWIHKLHKFLGSDEED
KDSLQELSTEQKCFVEHILCTRPLPCRQPAPIRGFWIVPDILGPTMICITSTYECLIWPLLSTVHP
ASPPLLCTREDVEVAESSLRVLAETPDSFEKHIRSILQRSVANPAFLKASEKDIAPPPEECLQLL
SRATQVFREQYILKQDLAKEEIQRRVKLLCDQKKKQLEDLSYCREERKSLREMAERLADKY
EEAKEKQEDIMNRMKKLLHSFHSELPVLSDSERDMKKELQLIPDQLRHLGNAIKQVTMKKD
YQQQKMEKVLSLPKPTIILSAYQRKCIQSILKEEGEHIREMVKQINDIRNHVNF.
```

8. The kit of claim 6 further comprising a control protein sample, which comprises the protein consisting of the amino acid sequence depicted in SEQ ID NO: 2 or an antigenic part thereof.

9. A method for identifying the presence of a malignant cancer cell comprising (a) providing a tissue biopsy sample; and (b) determining the level of expression in the tissue biopsy sample of a protein consisting of the amino acid sequence depicted in SEQ ID NO: 2 by contacting the sample with at least one of (i) a monoclonal antibody bearing the accession number DSM ACC 2457 and (ii) a recombinant or chimeric molecule that comprises at least six CDRs of the monoclonal antibody bearing the accession number DSM ACC 2457, which binds to the protein, wherein the tissue biopsy sample comprises a malignant cancer cell if the expression level of the protein is determined to be greater than the expression level of that protein in healthy or normal control tissue.

* * * * *

SEQUENCE LISTING

<160> NUMBER OF SEQ ID NOS: 2

<210> SEQ ID NO 1
<211> LENGTH: 2378
<212> TYPE: DNA
<213> ORGANISM: Homo sapiens

<400> SEQUENCE: 1

```
gataaaccca caagacacaa aacatacctt tcgagcagtt gggccaagat ggcggccgcc      60
gagggaccgg tgggcgacgg cgagctgtgg cagacctggc ttcctaacca cgtcgtgttc     120
ttgcggctcc gggagggact gaaaaaccag agtccaaccg aagctgagaa accagcttct     180
tcgtcgttgc cttcgtcgcc gccgccgcag ttgctgacga gaaacgtggt ctttggcctc     240
ggcggagagc ttttcctgtg ggacggagaa gacagctcct tcttagtcgt tcgccttcgg     300
ggccccagcg gcggcggcga agagcccgcc ctgtcccagt accagagatt gctttgcata     360
aatccacccc tgtttgaaat ctatcaagtc ttgttaagcc caacacaaca tcatgtagca     420
cttataggaa taaaaggact tatggtatta gaattaccta aaagatgggg gaagaattct     480
gaatttgaag gtgaaaatc aacagtgaat tgtagtacca ctccagttgc ggagagattt     540
ttcaccagtt ccacctctct gactctaaag catgctgcat ggtatccaag tgaaatcctg     600
gatccccacg tagtgctgtt aacatcagac aacgtaatca gaatttactc tctacgtgag     660
ccgcagacac ccactaacgt gataatactt tcagaagccg aagaggaaag tctagtactc     720
aataaaggaa gggcgtatac cgcatctcta ggagagacag cagttgcatt tgactttggg     780
ccattggacg cagtcccaaa gactctattt ggacaaaacg gcaaagatga agtagtggca     840
tacccactgt acatcttata tgaaaatgga gagactttcc tgacatacat cagtctgtta     900
cacagccctg gaaatatttg gaaagctgtt gggtccattg cccatgcatc tgcggctgaa     960
gataactatg gttatgatgc gtgtgctgta ctctgcttac cctgtgtccc caatatctta    1020
```

```
gtgatcgcta ctgaatcagg aatgctgtat cactgtgtcg tgctagaagg ggaagaagaa    1080
gatgaccaca cgtcagaaaa gtcctgggat tccaggattg acctcattcc ttctctgtat    1140
gtgtttgaat gtgttgagtt ggagcttgct ttgaaactgg catctggaga ggatgaccct    1200
tttgattctg actttttcttg tccagtcaaa cttcatagag atcccaagtg tccttcaaga   1260
tatcactgta ctcatgaagc tggtgtacat agtgttgggc taacttggat tcataaactt    1320
cacaaatttc ttggatcaga tgaagaagat aaggatagtt tacaggaact ctctacagaa    1380
cagaaatgct ttgttgaaca catcctttgt acgaggccat tgccctgcag gcagccagct    1440
ccaattcgag gattttggat tgtacctgac attctgggac ccacgatgat ctgcatcacc    1500
agtacctatg aatgcctcat atggccgtta ttaagtacag tccatccagc gtctcctccc    1560
ctgctttgta ctcgagaaga tgttgaagtg gcagagtctt ccctccgtgt tctggctgaa    1620
accccagatt cctttgaaaa gcatattaga agcattttgc aacgtagtgt tgccaatcca    1680
gcattttttga aagcttctga aaaggacata gcccctcctc ctgaagaatg ccttcagctc    1740
ctcagcagag ccacccaggt gttcagagag cagtacattc tcaaacagga cttggcaaag   1800
gaggagattc agcggagggt caaattatta tgtgaccaaa aaagaaaca actagaagat     1860
ctcagttatt gtcgagaaga gaggaaaagt ctgcgggaaa tggctgagcg tttagctgac   1920
aaatatgagg aagctaaaga aaaacaagag gatatcatga acaggatgaa aaaactactt   1980
cacagttttc actctgagct cccagttctc tctgatagtg agcgagacat gaagaaagaa   2040
ttacagctga tacctgatca acttcgacat ttgggcaatg ccatcaaaca ggttactatg   2100
aaaaaggatt atcaacagca aaagatggag aaggtgttga gtcttccaaa acccaccatt   2160
attctcagtg cctaccagcg aaagtgcatt cagtccatcc tgaaagagga gggtgaacat   2220
ataagggaaa tggtgaagca aatcaatgat atccgcaatc atgtaaactt ctgacaccac   2280
caggagctga ctcacacctg aactgaacac cattgaaggc ttaaacccat attgtaaaac   2340
aggtagaatt atctaattta taaaaggtg ttttgatg                             2378
```

<210> SEQ ID NO 2
<211> LENGTH: 741
<212> TYPE: PRT
<213> ORGANISM: Homo sapiens

<400> SEQUENCE: 2

Met Ala Ala Ala Glu Gly Pro Val Gly Asp Gly Glu Leu Trp Gln Thr
1               5                   10                  15

Trp Leu Pro Asn His Val Val Phe Leu Arg Leu Arg Glu Gly Leu Lys
                20                  25                  30

Asn Gln Ser Pro Thr Glu Ala Glu Lys Pro Ala Ser Ser Ser Leu Pro
            35                  40                  45

Ser Ser Pro Pro Gln Leu Leu Thr Arg Asn Val Val Phe Gly Leu
        50                  55                  60

Gly Gly Glu Leu Phe Leu Trp Asp Gly Glu Asp Ser Ser Phe Leu Val
65                  70                  75                  80

Val Arg Leu Arg Gly Pro Ser Gly Gly Glu Glu Pro Ala Leu Ser
                85                  90                  95

Gln Tyr Gln Arg Leu Leu Cys Ile Asn Pro Pro Leu Phe Glu Ile Tyr
            100                 105                 110

Gln Val Leu Leu Ser Pro Thr Gln His His Val Ala Leu Ile Gly Ile
        115                 120                 125

-continued

```
Lys Gly Leu Met Val Leu Glu Leu Pro Lys Arg Trp Gly Lys Asn Ser
    130                 135                 140

Glu Phe Glu Gly Gly Lys Ser Thr Val Asn Cys Ser Thr Thr Pro Val
145                 150                 155                 160

Ala Glu Arg Phe Phe Thr Ser Ser Thr Ser Leu Thr Leu Lys His Ala
                165                 170                 175

Ala Trp Tyr Pro Ser Glu Ile Leu Asp Pro His Val Val Leu Leu Thr
                180                 185                 190

Ser Asp Asn Val Ile Arg Ile Tyr Ser Leu Arg Glu Pro Gln Thr Pro
                195                 200                 205

Thr Asn Val Ile Ile Leu Ser Glu Ala Glu Glu Ser Leu Val Leu
    210                 215                 220

Asn Lys Gly Arg Ala Tyr Thr Ala Ser Leu Gly Glu Thr Ala Val Ala
225                 230                 235                 240

Phe Asp Phe Gly Pro Leu Asp Ala Val Pro Lys Thr Leu Phe Gly Gln
                245                 250                 255

Asn Gly Lys Asp Glu Val Val Ala Tyr Pro Leu Tyr Ile Leu Tyr Glu
                260                 265                 270

Asn Gly Glu Thr Phe Leu Thr Tyr Ile Ser Leu Leu His Ser Pro Gly
                275                 280                 285

Asn Ile Trp Lys Ala Val Gly Ser Ile Ala His Ala Ser Ala Ala Glu
    290                 295                 300

Asp Asn Tyr Gly Tyr Asp Ala Cys Ala Val Leu Cys Leu Pro Cys Val
305                 310                 315                 320

Pro Asn Ile Leu Val Ile Ala Thr Glu Ser Gly Met Leu Tyr His Cys
                325                 330                 335

Val Val Leu Glu Gly Glu Glu Asp Asp His Thr Ser Glu Lys Ser
                340                 345                 350

Trp Asp Ser Arg Ile Asp Leu Ile Pro Ser Leu Tyr Val Phe Glu Cys
    355                 360                 365

Val Glu Leu Glu Leu Ala Leu Lys Leu Ala Ser Gly Glu Asp Asp Pro
370                 375                 380

Phe Asp Ser Asp Phe Ser Cys Pro Val Lys Leu His Arg Asp Pro Lys
385                 390                 395                 400

Cys Pro Ser Arg Tyr His Cys Thr His Glu Ala Gly Val His Ser Val
                405                 410                 415

Gly Leu Thr Trp Ile His Lys Leu His Lys Phe Leu Gly Ser Asp Glu
                420                 425                 430

Glu Asp Lys Asp Ser Leu Gln Glu Leu Ser Thr Glu Gln Lys Cys Phe
    435                 440                 445

Val Glu His Ile Leu Cys Thr Arg Pro Leu Pro Cys Arg Gln Pro Ala
    450                 455                 460

Pro Ile Arg Gly Phe Trp Ile Val Pro Asp Ile Leu Gly Pro Thr Met
465                 470                 475                 480

Ile Cys Ile Thr Ser Thr Tyr Glu Cys Leu Ile Trp Pro Leu Leu Ser
                485                 490                 495

Thr Val His Pro Ala Ser Pro Leu Leu Cys Thr Arg Glu Asp Val
                500                 505                 510

Glu Val Ala Glu Ser Ser Leu Arg Val Leu Ala Glu Thr Pro Asp Ser
    515                 520                 525

Phe Glu Lys His Ile Arg Ser Ile Leu Gln Arg Ser Val Ala Asn Pro
530                 535                 540

Ala Phe Leu Lys Ala Ser Glu Lys Asp Ile Ala Pro Pro Pro Glu Glu
```

-continued

```
545              550              555              560
Cys Leu Gln Leu Leu Ser Arg Ala Thr Gln Val Phe Arg Glu Gln Tyr
            565              570              575

Ile Leu Lys Gln Asp Leu Ala Lys Glu Glu Ile Gln Arg Arg Val Lys
            580              585              590

Leu Leu Cys Asp Gln Lys Lys Lys Gln Leu Glu Asp Leu Ser Tyr Cys
            595              600              605

Arg Glu Glu Arg Lys Ser Leu Arg Glu Met Ala Glu Arg Leu Ala Asp
            610              615              620

Lys Tyr Glu Glu Ala Lys Glu Lys Gln Glu Asp Ile Met Asn Arg Met
625              630              635              640

Lys Lys Leu Leu His Ser Phe His Ser Glu Leu Pro Val Leu Ser Asp
            645              650              655

Ser Glu Arg Asp Met Lys Lys Glu Leu Gln Leu Ile Pro Asp Gln Leu
            660              665              670

Arg His Leu Gly Asn Ala Ile Lys Gln Val Thr Met Lys Lys Asp Tyr
            675              680              685

Gln Gln Gln Lys Met Glu Lys Val Leu Ser Leu Pro Lys Pro Thr Ile
            690              695              700

Ile Leu Ser Ala Tyr Gln Arg Lys Cys Ile Gln Ser Ile Leu Lys Glu
705              710              715              720

Glu Gly Glu His Ile Arg Glu Met Val Lys Gln Ile Asn Asp Ile Arg
            725              730              735

Asn His Val Asn Phe
            740
```